United States Patent [19]

Guigan

[11] Patent Number: 4,469,793

[45] Date of Patent: Sep. 4, 1984

[54] METHOD AND APPARATUS FOR DISPENSING A PREDETERMINED DOSE OF A SAMPLE LIQUID INTO A RECEPTOR CELL

[76] Inventor: Jean Guigan, 9, rue Jean Mermoz, 75008 Paris, France

[21] Appl. No.: 366,130

[22] Filed: Apr. 7, 1982

[30] Foreign Application Priority Data

Apr. 14, 1981 [FR] France .................................. 81 07437

[51] Int. Cl.³ .............................................. G01N 9/30
[52] U.S. Cl. ........................................ 436/45; 422/72; 422/100; 422/102; 436/180
[58] Field of Search ............... 222/144, 344, 253, 360, 222/361, 362, 359, 454; 193/20; 422/102, 104, 72, 100; 436/45, 180; 356/244, 246

[56] References Cited

U.S. PATENT DOCUMENTS

| 924,533 | 6/1909 | Compton et al. | 193/20 |
| 3,291,387 | 12/1966 | Billen | 422/72 |
| 3,901,658 | 8/1975 | Burtis | 422/104 |

*Primary Examiner*—H. Grant Skaggs
*Assistant Examiner*—Kenneth Noland
*Attorney, Agent, or Firm*—Sughrue, Mion, Zinn, Macpeak and Seas

[57] ABSTRACT

A rotor (1) for performing a chemical reaction such as biological analysis with a sample liquid comprises: a rotatable container (2) having a vertical axis of rotation; a radially inner basin having radial partitions (4) dividing the basin into a plurality of compartments (3) for receiving an approximately-determined volume of the sample liquid, the approximately-determined volume being greater than the predetermined dose; a plurality of receptor cells (5) regularly distributed around the periphery of the rotor for receiving the liquid in the predetermined doses; and radially intermediate apparatus for conveying the liquid from the compartments to corresponding receptor cells under the effect of centrifugal force when the rotor is caused to rotate. The radially intermediate apparatus includes dispensing predetermined doses, which apparatus comprises, between each compartment (3) in the basin and a corresponding receptor cell (5), a measurement chamber (7) having an inlet orifice (6) in communication with the compartment (3), and an outlet orifice (8). The inlet and outlet orifices delimit a volume corresponding to the predetermined dose. The outlet orifice (8) leads passages (9, 10) responsive to the direction of rotation of the rotor to direct liquid issuing therefrom either to an overflow chamber (11) when the rotor is rotating in a first direction (A), or else to the receptor cell (5) when the rotor is rotating in a second, opposite direction (B).

14 Claims, 10 Drawing Figures

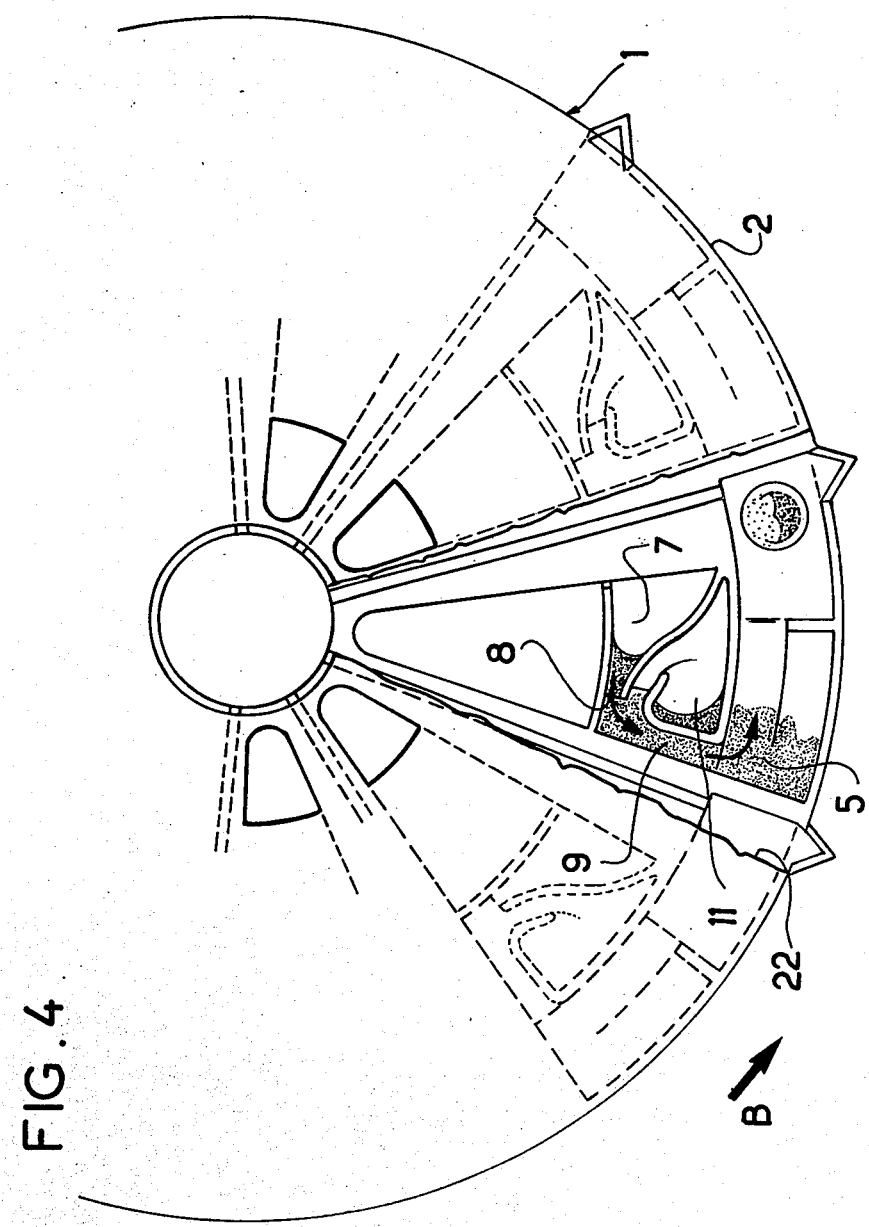

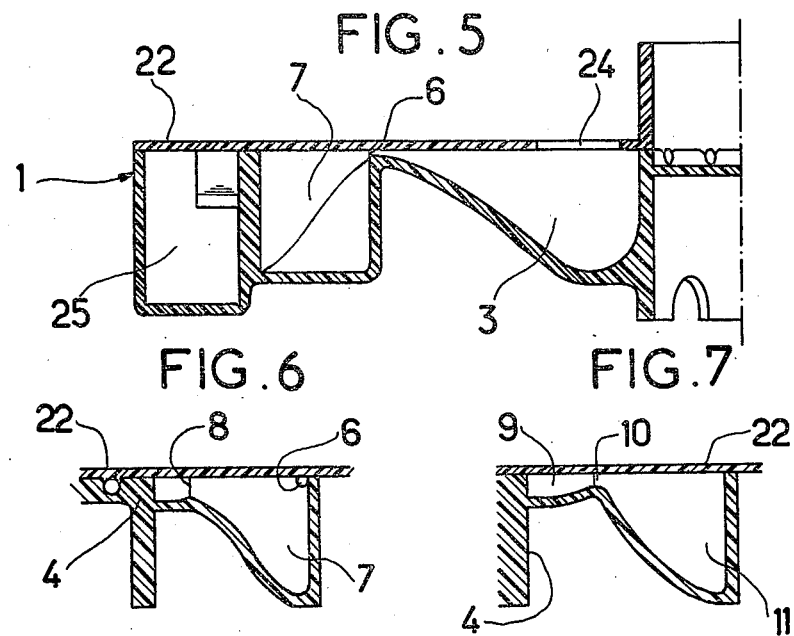
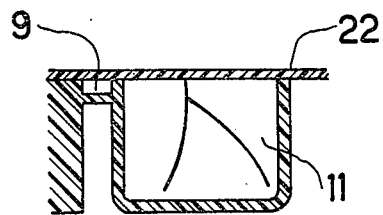
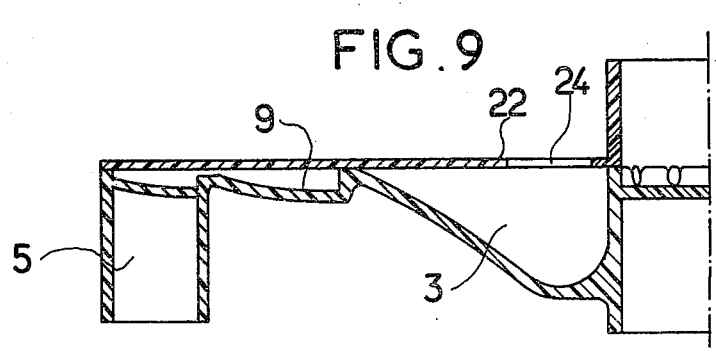

METHOD AND APPARATUS FOR DISPENSING A PREDETERMINED DOSE OF A SAMPLE LIQUID INTO A RECEPTOR CELL

The present invention relates to apparatus for dispensing a predetermined dose of a sample of liquid into a receptor cell on a rotor, for the purpose of performing a chemical reaction with the liquid, eg. performing a biological analysis thereof. A rotatable disk with a vertical axis of rotation is used for such analysis. It has an annular basin split up by radial partitions into compartments for receiving the sample liquid. A plurality of receptor cells are arranged regularly around the periphery of the disk and radially intermediate means are provided for conveying the liquid from the annular basin to the peripheral cells under the effect of centrifugal force generated by spinning the disk about its axis. The dosing is performed by said intermediate means.

BACKGROUND OF THE INVENTION

In known apparatus, the receptor cells are filled with a predetermined quantity of a sample liquid by filling each of the compartments from a pipette. When the rotor is subsequently spun, the liquid contained in the various compartments moves outwardly towards the associated receptor cells. However, the apparatus cannot work for long unattended, since it must be moved to under a pipette in order to refill its verious compartments.

Preferred embodiments of the present invention mitigate this drawback.

SUMMARY OF THE INVENTION

The present invention provides apparatus for dispensing a predetermined dose of a sample liquid into a receptor cell on a rotor for performing a chemical reaction with said liquid, said rotor comprising: a rotatable container having a vertical axis of rotation; a radially inner basin having radial partitions dividing said basin into a plurality of compartments for receiving an approximately-determined volume of said sample liquid, said approximately-determined volume being greater than said predetermined dose; a plurality of receptor cells regularly distributed around the periphery of said rotor for receiving said liquid in said predetermined doses; and radially intermediate means for conveying said liquid from said compartments to corresponding receptor cells under the effect of centrifugal force when said rotor is caused to rotate, said radially intermediate means including said apparatus for dispensing said predetermined doses; wherein said apparatus comprises, between each compartment in said basin and a corresponding receptor cell, a measurement chamber having an inlet orifice in communication with said compartment, and an outlet orifice, said inlet and outlet orifices delimiting a volume corresponding to said predetermined dose, and said outlet orifice leading to means responsive to the direction of rotation of the rotor to direct liquid issuing therefrom either to an overflow chamber when said rotor is rotating in a first direction, or else to said receptor cell when said rotor is rotating in a second, opposite direction.

The outlet orifice is preferably a capillary orifice.

Said means responsive to the direction of rotation preferably comprise an outflow channel extending substantially radially from said outlet orifice to said receptor cell, said outflow channel being provided with a branch leading from a point immediately downstream from said outlet orifice and on the same side of said outflow channel as said outlet orifice to said overflow chamber.

Advantageously, the apparatus includes at least one of the following features:

(a) the wall of said outflow channel, at least in the vicinity of said branch is curved in such a manner as to prevent any liquid from flowing into said branch when said rotor is rotating in said second direction.

(b) said outlet orifice putting said measurement chamber into communication with said outflow channel is situated adjacent one of said radial partitions such that rotating said rotor in said direction drives liquid contained in said measurement chamber towards said partition.

(c) said overflow chamber is shaped in such a manner that liquid which enters therein during rotation in said first direction is retained therein during rotation in said second direction.

(d) said overflow chamber has a curved wall portion with said branch from said outflow channel opening out in the top part of said curved wall portion.

(e) said inlet orifice putting said measurement chamber in communication with said compartment in said basin is located adjacent to that one of said radial partitions against which the liquid is thrust by rotating said rotor in said first direction.

(f) said compartment in said basin has a curved wall portion with said inlet orifice to said measurement chamber being located near the top part of said curved wall portion.

(g) said measurement chamber has a curved wall portion with said outlet orifice being located near the top part of said curved wall portion.

(h) said basin is divided into a plurality of compartments each of which supplies said liquid to a plurality of receptor cells.

(i) said receptor cell is used as a reaction cell and is provided with a top wall having an air vent orifice.

(j) said receptor cell is used as a pouring cell for pouring said liquid into a reaction cell, said reaction cell being provided with a peripheral liquid ejection orifice which also serves as an air vent.

The invention also provides a method of dispensing a predetermined dose of a sample liquid into receptor cell, using the above defined apparatus, wherein a volume of said sample liquid is inserted into a compartment of said basin, said volume being greater than said predetermined dose, said rotor is then rotated in said first direction emptying all said liquid from said compartment into the or each measurement chamber which is in communication therewith via said inlet orifice(s), thereby completely filling the or each measurement chamber, with the excess liquid leaving via said outlet orifice(s) and entering said overflow chamber(s), and finally rotating said rotor in said second or opposite direction thereby moving all the liquid contained in said measurement chamber(s) into the receptor cell(s).

BRIEF DESCRIPTION OF THE DRAWINGS

Two embodiments of the invention are described by way of example with reference to the accompanying drawings, in which:

FIGS. 2, 3 and 4 are views similar to FIG. 1, showing successive stages in the use of the apparatus.

FIG. 5 is a cross section along line V—V of FIG. 1.

FIG. 6 is a cross section along line VI—VI of FIG. 1.

FIG. 7 is a cross section along line VII—VII of FIG. 1.

FIG. 8 is a cross section along line VIII—VIII of FIG. 1.

FIG. 9 is a cross section along line IX—IX of FIG. 1.

MORE DETAILED DESCRIPTION

Figure 1:
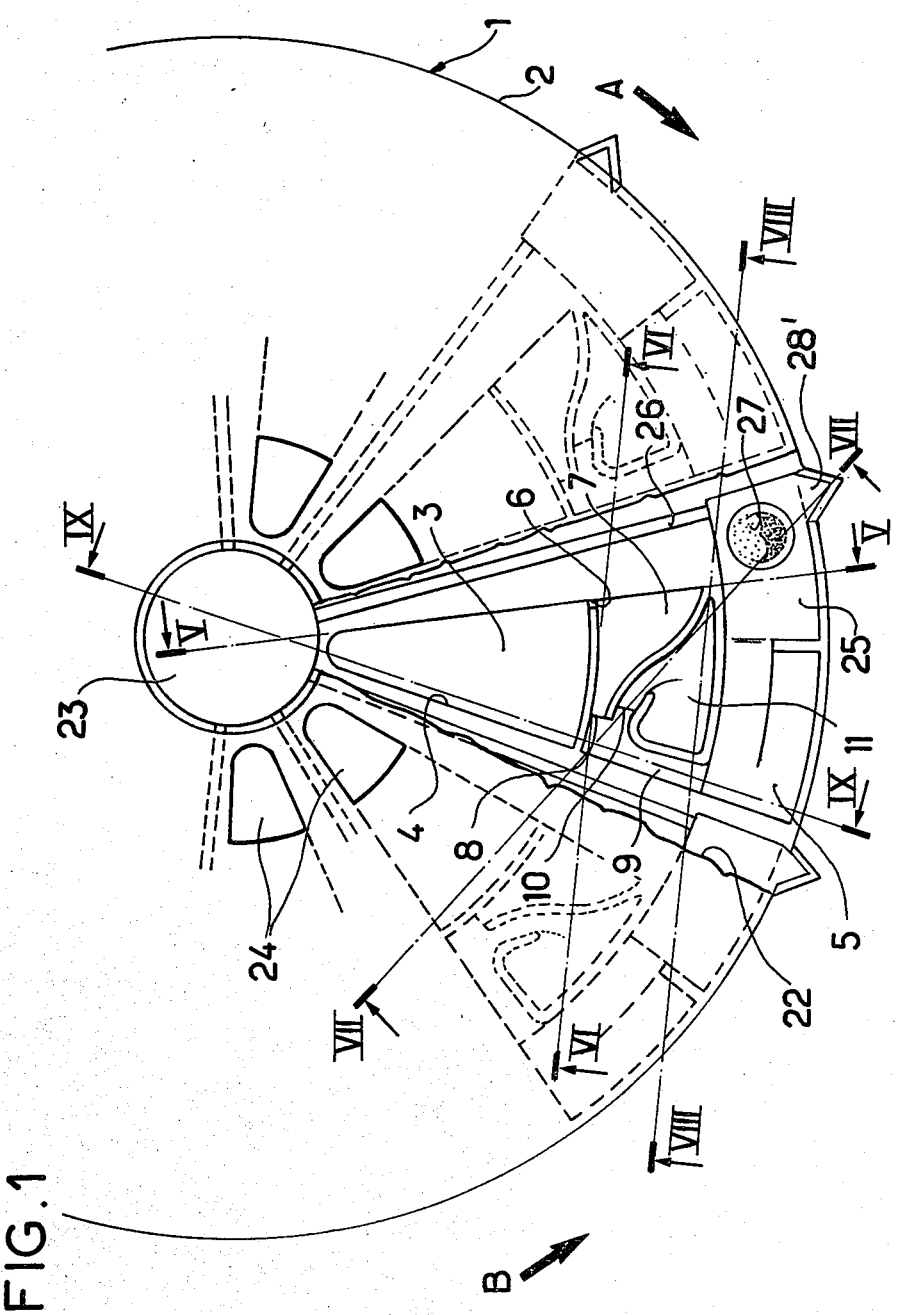
FIG. 1 is a diagrammatic and partially cut away plan view from above of apparatus in accordance with the invention.

In the figures the rotor disk is generally designated 1. It comprises a container 2 having a vertical axis and provided with a cover 22. Inside the container there are compartments 3 formed by radial partitions 4 which subdivide an annular basin.

There is a central orifice 23. The cover 22 has openings 24 for filling the compartments 3.

At the periphery of the container 2 there are receptor cells such as 5, which are regularly distributed around the annular basin. The entire system is made of transparent plastics material and may be rotated by any suitable means.

In the embodiment shown in the drawings and shown by way of example, the receptor cells 5 are associated with respective analysis cells 25 in communication therewith. The analysis cells 25 are connected to the central orifice 23 by respective channels 26. This arrangement of associated cells has already been described in French patent application number 80 26528 filed on Dec. 15, 1980 by the present Applicant. In the analysis cells 25, there are reaction supports, eg. beads 27.

In accordance with the invention, the compartment 3 is in communication with a measurement chamber 7 via an orifice 6 referred to as an inlet orifice.

The measurement chamber 7 also has a second orifice 8, referred to as an outlet orifice.

Advantageously, the second or outlet orifice 8 is a capillary orifice.

The orifice 8 leads to an outflow channel 9 emptying into a receptor cell 5.

The channel 9 is substantially radial and immediately downstream from the outlet orifice 8 it has a branch 10 leading to an overflow chamber 11.

The measurement chamber 7 and the branch 10 are situated on the same side of the outflow channel 9.

Figure 2:
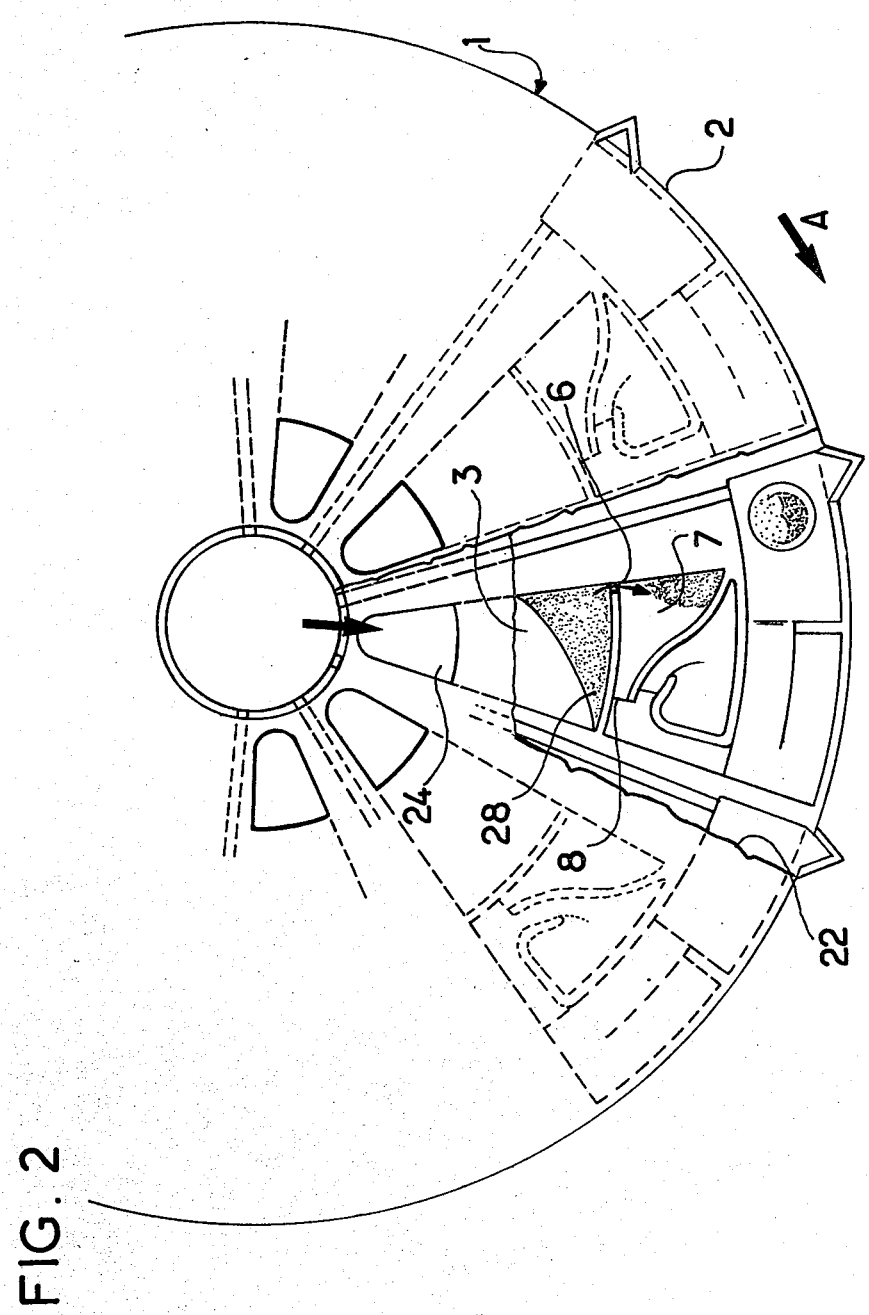
Figure 3:
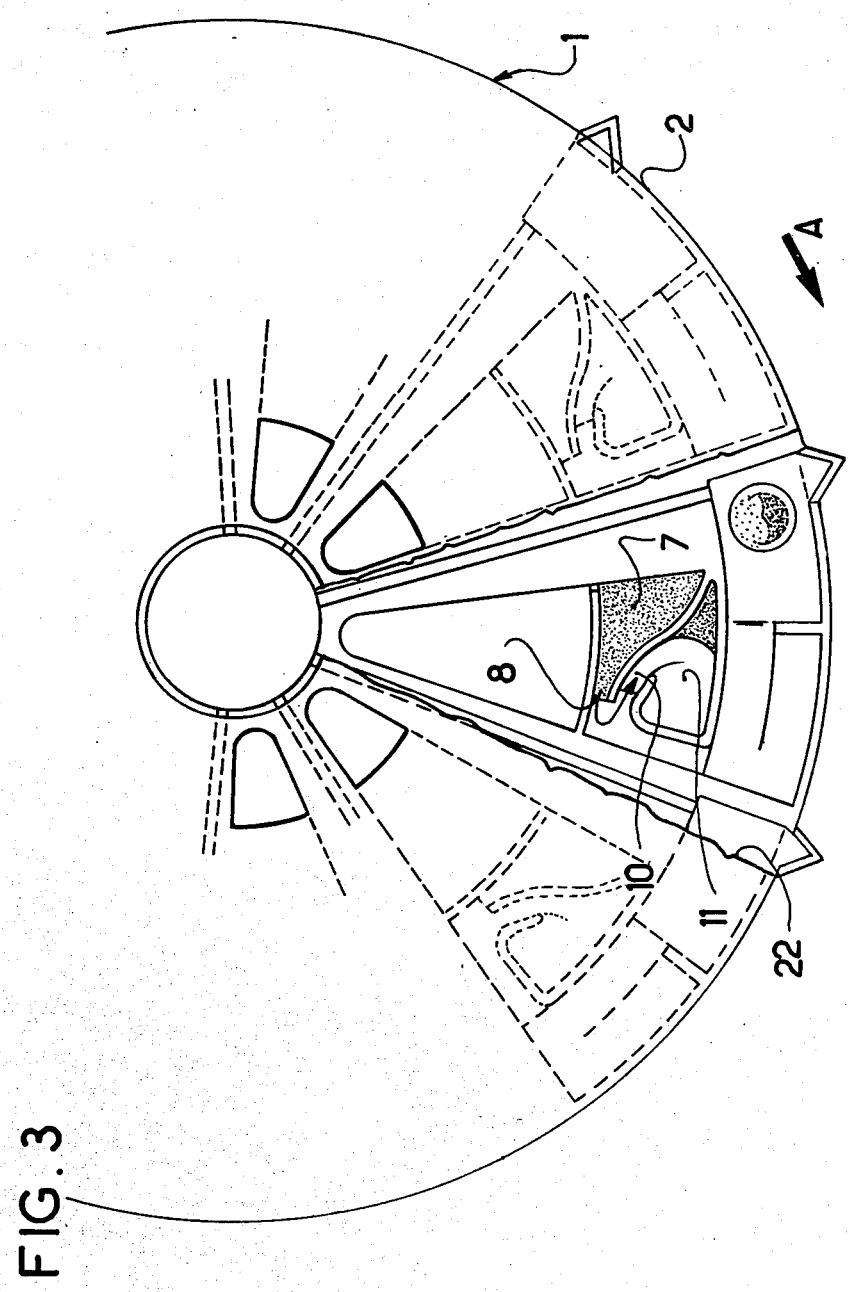

Operation is as follows:

A certain quantity of sample liquid 28, ie. a greater volume than can be contained in the measurement chamber 7, is inserted into a compartment 3 via its opening 24. The rotor 1 is then made to rotate in the direction of the arrow A (see FIG. 2). Under the effect of centrifugal force, the liquid contained in the compartment 3 is propelled into the measurement chamber 7 via its inlet orifice 6. The rotation in the direction of the arrow A continues, and after the measurement chamber 7 has been completely filled, excess liquid driven out from the measurement chamber 7 via its outlet orifice 8 flows into the overflow chamber 11 following the branch 10, which is located for this purpose in the immediate vicinity of the outlet orifice 8 (see FIG. 3).

At this point in the procedure, the rotor is made to rotate in the opposite direction as shown by an arrow B in FIG. 4. All the liquid contained in the measurement chamber 7 is expelled therefrom via the outlet orifice 8 and flows along the outflow channel 9 to the receptor cell 5. Meanwhile, the excess liquid present in the overflow chamber 11 is retained therein as can be seen on FIG. 4. In a variant, the overflow chamber 11 could be provided with an evacuation orifice whereby the excess liquid could be directed to some suitable receptacle.

It can thus be seen that implementing the apparatus and the method associated therewith in accordance with the invention, makes it possible to dispense a predetermined dose of sample liquid into the receptor cell 5, said dose being determined by the volume of the measurement chamber 7.

By way of example, the measurement chamber may have a volume of 100 microliters, with the overflow chamber having a volume of about 50 microliters. In such a case, the volume of sample liquid initially inserted in the compartment 3 should be about 130 microliters.

As can be observed with reference to FIG. 5, which is a section along a radial partition, the profile of the compartment 3 which initially receives the sample liquid is curved, with the inlet orifice 6 to the measurement chamber 7 being situated near to the top of the said curved profile. Further, as can be seen with reference to FIG. 2, the inlet orifice 6 is situated close to one of the partitions 4 which delimit the compartment 3, in particular close to that one of the partitions towards which the liquid moves in the compartment 3 when the rotor is made to rotate in the direction of the arrow A.

The measurement chamber 7 also has a curved profile, with the outlet orifice 8 being situated close to the top of the curved profile, as can be seen in FIG. 6 which is a section through the orifice 8.

FIG. 7 is a section passing substantially along the axis of the branch 10. Near to this branch, the wall of the outflow channel 9 is slightly curved in such a manner as to avoid liquid going from the measurement chamber 7 into the overflow chamber 11 when the rotor is rotating in the direction of the arrow B.

On FIG. 7, it can also be observed that the overflow chamber 11 has a curved profile, with the branch 10 coming from the outflow channel 9 opening out near the top of said curving portion.

FIG. 8 is a section along a line VIII—VIII of FIG. 1, to show up the shape of the overflow chamber 11. It includes a portion in which the overflow is received while the rotor is turning in the direction of the arrow A and another portion in which the overflow is received when the rotor is turning in the opposite direction as indicated by the arrow B.

The overflow chamber could also be provided with an evacuation orifice so as to remove the overflow liquid after rotation in the direction of the arrow A, as has already been mentioned above.

As shown in FIG. 6, the outlet orifice 8 which puts the measurement chamber 7 in communication with the outflow channel 9 is situated near to that one of the radial partitions 4 against which the liquid in the measurement chamber 7 is thrust when the rotor is rotated in the direction of the arrow B.

FIG. 9 is a cross section substantially along the axis of the outflow channel 9.

It is immaterial for the invention, whether the compartments in the annular basin are used to supply liquid to one or to several measurement chambers.

Figure 10:
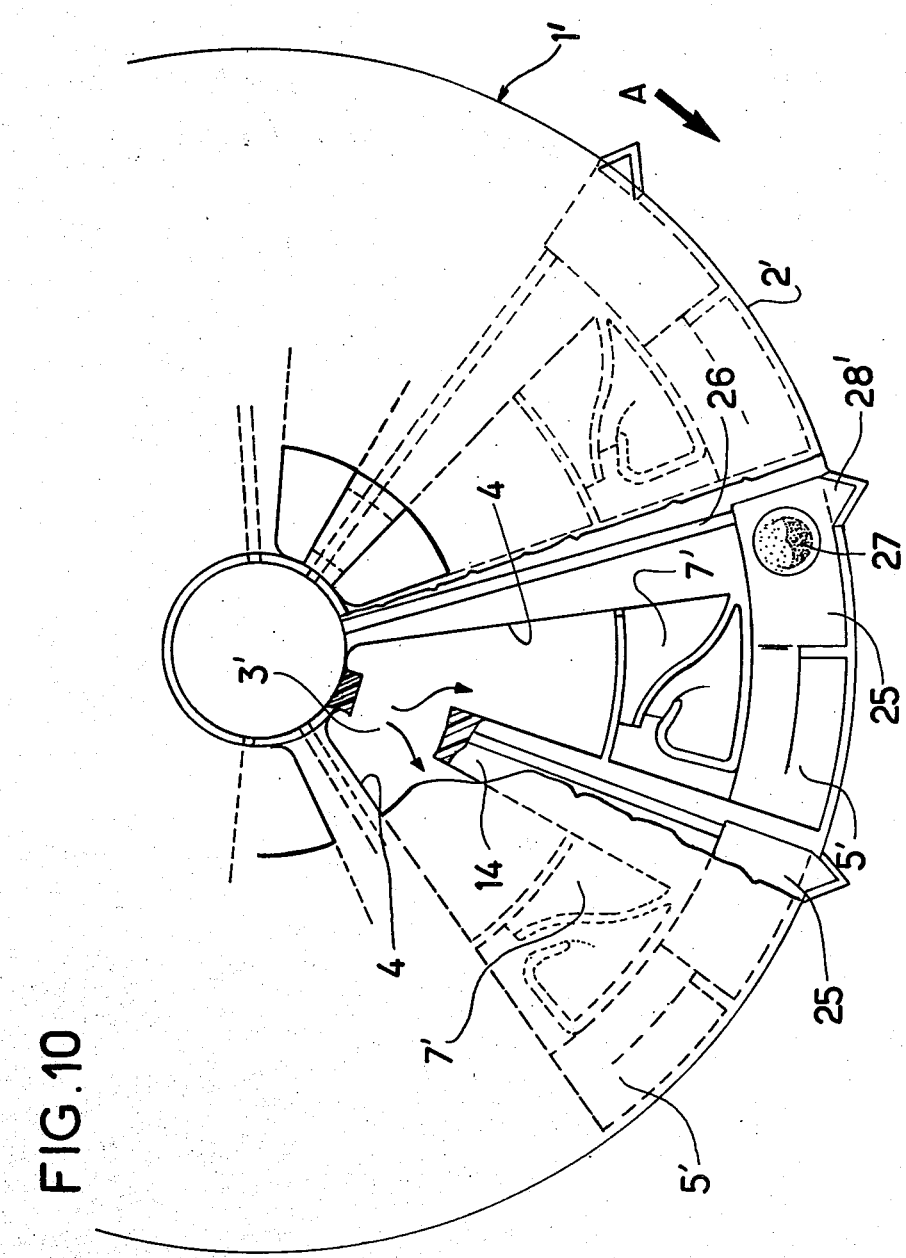
FIG. 10 is a view similar to FIG. 1, showing a second embodiment.

Such an embodiment is shown diagrammatically in FIG. 10 where a single compartment 3' is arranged to supply liquid to two receptor cells 5'. An in between radial partition 14 serves to distribute the liquid to both measurement chambers 7' when the rotor 1' is made to rotate in the direction of the arrow A.

In the examples shown and described, the receptor cells are used as pouring cells and they pour liquid into the analysis cells 25 which include peripheral ejector orifices 28' for ejecting both liquid and air.

The solid reactor support, eg. the bead 27, is intended to pick up successively a quantity of a compound such as a biological liquid containing a substance to be analysed, then a quantity of a first reagent in which a biological indicator is fixed.

The channels 26 serve to convey a washing liquid to each of the analysis cells 25 associated with their corresponding pouring cells which receive the compound containing the substance to be analysed, said associated cells communicating via an orifice.

Clearly the various comparments on a single rotor can be supplied with samples of different liquids, and in this case the apparatus in accordance with the invention can be used for simultaneous analyses.

Further, the receptor cells may be used directly as analysis cells in some applications. In this case, it is necessary to provide air venting orifices in these cells.

It will readily be appreciated that the invention is not limited to the specific embodiments described in detail above by way of example.

I claim:

1. Apparatus for dispensing a predetermined dose of a sample liquid for performing a chemical reaction with said liquid, said apparatus comprising:
   a rotor including a rotatable containing having a vertical axis of rotation;
   a radially inner basin having radial partitions dividing said basin into a plurality of compartments for receiving an approximately-determined volume of said sample liquid, said approximately-determined volume being greater than said predetermined dose;
   a plurality of receptor cells regularly distributed around the periphery of said rotor for receiving said liquid in said predetermined doses; and
   means for converying said liquid radially from said compartments to corresponding receptor cells under the effect of centrifugal force when said rotor is caused to rotate;
   and wherein said apparatus comprises, between each compartment in said basin and a corresponding receptor cell, a measurement chamber having an inlet orifice in communication with said compartment, and an outlet orifice, and an overflow chamber, said inlet and outlet orifices delimiting a volume corresponding to said predetermined dose, and wherein said outlet orifice leads to means responsive to the direction of rotation of the rotor to direct liquid issuing therefrom either to said overflow chamber when said rotor is rotating in a first direction, or else to said receptor cell when said rotor is rotating in a second, opposite direction.

2. Apparatus according to claim 1, wherein said means responsive to the direction of rotation to direct liquid comprises an outflow channel extending substantially radially from said outlet orifice to said receptor cell, said outflow channel being provided with a branch leading from a point immediately downstream from said outlet orifice and on the same side of said outflow channel as said outlet orifice to said overflow chamber.

3. Apparatus according to claim 2, wherein said outflow channel includes a wall, and said wall, at least in the vicinity of said branch is curved in such a manner as to prevent any liquid from flowing into said branch when said rotor is rotating in said second direction.

4. Apparatus according to claim 2, wherein said outlet orifice putting said measurement chamber into communication with said outflow channel is situated adjacent one of said radial partitions such that rotating said rotor in said direction drives liquid contained in said measurement chamber towards said partition.

5. Apparatus according to claim 2, wherein said overflow chamber is shaped in such a manner that liquid which enters therein during rotation in said first direction is retained therein during rotation in said second direction.

6. Apparatus according to claim 2, wherein said overflow chamber has a curved wall portion including a top part with said branch from said outflow channel opening in said top part of said curved wall portion.

7. Apparatus according to claim 1, wherein said inlet orifice putting said measurement chamber in communication with said compartment in said basin is located adjacent to that one of said radial partitions against which the liquid is thrust by rotating said rotor in said first direction.

8. Apparatus according to claim 1, wherein said compartment in said basin has a curved wall portion including a top part with said inlet orifice to said measurement chamber being located near said top part of said curved wall portion.

9. Apparatus according to claim 1, wherein said measurement chamber has a curved wall portion with said outlet orifice being located near the top part of said curved wall portion.

10. Apparatus according to claim 1, wherein said basin is divided into a plurality of compartments each of which supplies said liquid to a plurality of receptor cells.

11. Apparatus according to claim 1, wherein said receptor cell is used as a reaction cell and is provided with a top wall having an air vent orifice.

12. Apparatus according to claim 1, wherein said receptor cell is used as a pouring cell for pouring said liquid into a reaction cell, said reaction cell being provided with a peripheral liquid ejection orifice which also serves as an air vent.

13. Apparatus according to claim 1, wherein said overflow chamber includes an orifice for evacuating liquid therefrom.

14. A method of dispensing a predetermined does of a sample liquid into a rotor receptor cell, said method comprising the steps of:
   inserting a volume of said sample liquid into a compartment of a basin, said volume being greater than said predetermined dose,
   rotating said rotor in a first direction for emptying all said liquid from said compartment into a measurement chamber which is in communication therewith via an inlet orifice, thereby completely filling the measurement chamber,
   causing the excess liquid to leave the measurement chamber via an outlet orifice and to enter an overflow chamber, and
   finally rotating said rotor in a second, opposite direction thereby moving all the liquid contained in said measurement chamber into the receptor cell.

* * * * *